(12) United States Patent
Westmoreland et al.

(10) Patent No.: US 9,476,743 B1
(45) Date of Patent: Oct. 25, 2016

(54) PROBE WITH NO MOVING PARTS FOR USE IN A TANK

(71) Applicant: INNOVATIVE MEASUREMENT METHODS, INC., Sugar Land, TX (US)

(72) Inventors: Allen Ray Westmoreland, Sugar Land, TX (US); John Charles Hoben, Sugar Land, TX (US); Alexander Bukhman, Sugar Land, TX (US); Yosef Brodsky, Sugar Land, TX (US)

(73) Assignee: INNOVATIVE MEASUREMENT METHODS, INC., Sugar Land, TX (US)

( * ) Notice: Subject to any disclaimer, the term of this patent is extended or adjusted under 35 U.S.C. 154(b) by 0 days.

(21) Appl. No.: 15/041,821

(22) Filed: Feb. 11, 2016

(51) Int. Cl.
| | |
|---|---|
| *G01F 1/34* | (2006.01) |
| *G01N 9/26* | (2006.01) |
| *G01F 23/14* | (2006.01) |
| *G01N 25/00* | (2006.01) |
| *G01N 7/00* | (2006.01) |
| *G01N 33/28* | (2006.01) |
| *G01G 17/04* | (2006.01) |
| *G01C 9/00* | (2006.01) |

(52) U.S. Cl.
CPC . *G01F 1/34* (2013.01); *G01C 9/00* (2013.01); *G01F 23/14* (2013.01); *G01G 17/04* (2013.01); *G01N 7/00* (2013.01); *G01N 9/26* (2013.01); *G01N 25/00* (2013.01); *G01N 33/2847* (2013.01)

(58) Field of Classification Search
None
See application file for complete search history.

(56) References Cited

U.S. PATENT DOCUMENTS

| | | | | |
|---|---|---|---|---|
| 4,855,714 A | * | 8/1989 | Clarkson | G08B 19/00 340/521 |
| 2003/0029236 A1 | * | 2/2003 | Morgan | G01F 22/00 73/149 |
| 2016/0091357 A1 | * | 3/2016 | Hedtke | G01F 23/284 342/124 |

* cited by examiner

*Primary Examiner* — Aditya Bhat
(74) *Attorney, Agent, or Firm* — Buskop Law Group, PC; Wendy Buskop (57) ABSTRACT

A probe with no moving parts for use in a tank having pressure transducers, temperature sensors, a probe processor electrically connected to the pressure transducers and the temperature sensors, and a probe data storage. The probe controls the temperature sensors and the pressure transducers to produce bidirectional signals and calculate at least one physical property, and perform adaptive measurement for synchronized measurement of the fluid in static operation, non-synchronized measurement of the fluid in static operation, non-synchronized measurement of the fluid in dynamic operation, synchronized measurement of the fluid in dynamic operation, and combinations thereof. The probe data storage contains computer instructions to instruct the probe processor to identify temperature sensors and pressure transducers not covered by the fluid, measure movement of the fluid in the tank, calibrate pressure transducers of the tank, and communicate with a client device via a network using bidirectional signals.

16 Claims, 6 Drawing Sheets

PROBE WITH NO MOVING PARTS FOR USE IN A TANK

FIELD

The present embodiments generally relate to a probe for measuring fluids in vessels, such as above ground tanks or below ground tanks.

BACKGROUND

A need exists for a highly sensitive monitoring probe that incorporates synchronized sensing devices for increased accuracy in measurements.

The present embodiments meets these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The embodiments relate to a land based probe with no moving parts for use in a tank.

The present embodiments can have the benefit of being a detection and monitoring apparatus that can monitor emissions from vessels, such as tanks, and can compare the measured emission to requirements of environmental laws and regulations.

The present embodiments can provide multiple sensors and multiple pressure transducers for performing hydrostatic tank measurements and can provide increased accuracy and consistency with regard to measurement values.

Specific structural and functional details disclosed herein are not to be interpreted as limiting, but merely as a basis of the claims and as a representative basis for teaching persons having ordinary skill in the art to variously employ the present embodiments.

In embodiments, the probe can be used for measuring fluid in a vessel, such as a tank, a truck with a tank, above ground tanks, and below ground tanks. The below ground tanks can include cut-and-cover tanks of larger storage volume or caverns.

The term "fluid" as used herein can include liquids, gasses with or without contaminants or impurities, and combinations thereof. Vapor pressure can be used in the conventional manner and can be included within the scope of the term "gas" for this application. Fluids can include hydrocarbons, water, wine, beer, gasoline, oil, pharmaceuticals, alcohols, esters, inert gasses and vapors.

The term "fluid temperature" as used herein can refer to an average fluid temperature or a multipoint spot temperature of the fluid.

The term "pressure transducer" as used herein can refer to a device that can measure pressure of the fluid.

The term "processor" as used herein can be a laptop, a cellular phone or a smart phone, a desktop computer, a server on a network, a measuring device that does different measuring and can connect to the plurality of temperature sensors and the plurality of pressure transducers, and combinations thereof. The processor can be in wired or wireless communication with the temperature sensors and the pressure transducers.

The term "data storage" refers to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals.

The term "simultaneously' as used herein can mean the temperature sensors and pressure transducers can collect measured data at the same time or within a few milliseconds of each other, such as a period ranging from zero to one hundred milliseconds.

The term "temperature sensor" as used herein can refer to a temperature sensor for detecting a temperature of a fluid in a tank.

The term "tank" as used herein can refer to a wide variety of tanks and containers that can hold fluids including separators, storage tanks, container trucks, or vats. For example, tanks can include a tank containing ten barrels of oil or 1,000,000 barrels of oil. The tanks can be structured with or without floating roofs. The tanks can have any shape, including circular shapes, square shapes or other similar shapes. Tanks of any volume can be made from various materials.

The embodiments can provide the benefit of continuous measurements, which can be simultaneous with the comparison of measured values with preset limits, such as environmental standards.

The embodiments can provide enhanced accuracy and consistent measurement over existing detection and monitoring apparatus.

The embodiments can identify numerous physical characteristics that can be measured using the temperature sensors and the pressure transducers for the gas or liquid, which can be with or without particulate matter.

Use of the present invention can prevent hazardous environmental emissions and can avoid other potentially dangerous or detrimental fluid conditions through continuous monitoring.

The comparison of measurements with preset limits can allow remediation to be taken when fluid conditions reach unacceptable levels, thereby preventing environmental contamination, explosions, loss of fluid, death and damage to equipment.

Unacceptable levels can be extreme pressure and temperatures, the formation of vacuums, and the emissions of harmful amounts of hydrocarbons and other potentially harmful chemicals.

For example, a calculated value, such as a mass of a fluid, can range from a few tons to thousands of tons of crude oil in an oil tank farm. A calculated value, such as a fluid volume in a tank, can range from tens of barrels to millions of barrels of liquid petroleum gas. Fluid density can range from 0.5 g/cm³ to 2 g/cm³ or more for most petroleum products.

Temperature of the fluid can range from −60 degrees Centigrade to 200 degrees Centigrade. Temperature of the fluid can include vapor temperatures in addition to liquid temperature measurement. Impurity of the fluid can include detection of water in oil on a percentage basis, such as a 5 percent impurity in West Texas crude oil.

In embodiments, one or more of the pressure transducers can include a diaphragm. The diaphragm can be oriented horizontal to the bottom of the tank. The diaphragm can also be at other orientations.

In embodiments, the temperature sensors or the pressure transducers can provide an analog signal to a probe processor. The analog signal can be digitized, such as by use of an analog-to-digital converter. The analog signal can be stored in a fixed data storage or a removable data storage, transmitted to a remote data storage or another processor, or combinations thereof.

In embodiments, the probe can use temperature sensors and pressure transducers with built-in processors and directing digital communications to the probe processor. That is, each temperature sensor and each pressure transducer can communicate with a probe processor. The probe processor can then wirelessly communicate or make a wired connection to a network with a remote processor and remote data storage, such as a cloud processing system.

In an embodiments, the probe cannot use an analog to digital converter between the pressure transducers, the temperature sensors, and one or more probe processors of a tank.

In embodiments, the remote processor can receive data from a tank via the network to create virtual gauges for the tank.

A particular example of the probe can use the temperature sensors and pressure transducers in a long row, such as an array. Each temperature sensor and pressure transducers can have a sequential number from 1 to 10. In this embodiment, the temperature sensors numbering 1, 3, 5, 7, and 9 can communicate with a processor "A". The temperature sensors with numbers 2, 4, 6, 8, and 10 can communicate with a processor "B". This alternating measurement using multiple processors continuously can provide for the extreme high accuracy and reliability of measurement with this device.

The synchronization of the pressure transducers can be established using a clock or a timed device with the processor or internal to the processor. Pressure transducers, electronic switches and signals, analog-to-digital converters, and other equipment connected to the probe can be synchronized for increased accuracy.

In embodiments, the probe processor can synchronously poll measurement data from the temperature sensors and the pressure transducers simultaneously and calculate values, which can form calculated values. For example, fluid density can be difficult to measure in a moving fluid without using synchronized data.

In embodiments, the probe processor can convert pressure and temperature sensor data to one or more values using computer instructions with models and other computations stored in memory or associated data storage. The values can provide a reading or notification for leak detection and related measurement including unauthorized movement of fluid from the tank.

The calculated values can be compared to one or more predetermined ranges of values for the fluid to identify whether the calculated values are within the predetermined ranges. For example, a density of a specific crude oil can have a predetermined range from 0.85 to 1.0 g/cm3, and the present apparatus can continuously collect data and compare the collected data to that predetermined range. Notification can be provided if the calculated values exceed a predetermined range. Use of automated responses, such as alarms, can be used when the calculated values exceed a predetermined range.

The calculated values can include a mass of the fluid, a fluid volume, an average temperature of the fluid, a multiple density strata of the fluid, an average density of the fluid, a level of the fluid, a fluid flow rate, an impurity content of the fluid, an entrained water content of the fluid, a free water content of the fluid, or combinations thereof.

In embodiments, the invention can monitor and compare measurements for atmospheric or ambient pressures and temperatures to measurements for vapor pressures and vapor temperatures, which can provide data with notifications and/or alarms. Examples of these types of data can include extreme pressures, extreme temperatures, the formation of vacuums, high amounts of hydrocarbon emissions or other harmful chemical emissions, or combinations thereof. Immediate notifications and alarms can be produced to provide an alert of potentially harmful gasses, liquids, and vapors that are escaping into the atmosphere and surrounding area.

In embodiments, the probe processor can communicate compared values to a data collector. The data collector can include one or more data storage media in communication with the processor, which can include remote data storage media, removable data storage media, and fixed data storage media.

The remote processor can communicate with one or more of the following: (1) a remote terminal unit, such as a Bristol Babcock RTU for tubular line monitoring, (2) a distributive control system, such as, a Honeywell DSC 3000, (3) a supervised control and data acquisition (SCADA) system, such as a Human Machine Interface system, (4) another computer, (5) another a tank or vessel gauge interface unit, such as a 1515 ETGI provided by Gauging Systems, Inc. of Houston, Tex., and other similar devices.

In embodiments, communication of the compared values to the remote processor can be performed using a field wiring bus, a network, or combinations thereof. Networks can include the internet, a local area network, a radio network, a hard wired network, a copper wire network, a cellular network, a satellite network, a fiber optic network, an infrared connection, a plain old telephone system (POTS), other wireless or wired networks, and combinations thereof.

In an embodiment, the temperature sensors and the pressure transducers can each include a transmitter, such as a radio transceiver, a satellite transmitter, a cellular transceiver, an RS-485 wired transmitter, or other similar transmitters. The transmitter can communicate between the temperature sensors and the pressure transducers and the remote processor. This communication can be a wireless communication, such as an infrared, satellite, or cellular communication, a fiber optic communication, a cabled communication, or combinations thereof.

The invention can include a sensor housing for containing temperature sensors and pressure transducers. The sensor housing can be made from any durable material, including machined stainless steel, plastic, a metal alloy, such as HASTELLOY-C™, TEFLON™, aluminum, KYNAR™ composites, ceramic composites, and formed polymer blends, such as PVC.

In an embodiment, the invention can include one or more channels. The channels can contain signaling wires to convey temperature sensor data to the probe processor. The channels can be smooth walled and can enable continuous communication of the temperature sensors and the pressure transducers with the processor. The signaling wires can be multi-conductor wire, such as wire available from Belden, other types of wire, or similar communication wiring, such as fiber optic wiring or cable.

In an embodiment, the invention can be installed into or in proximity to a gauge well or gauge hatch of a large tank, such as an oil tank, so that uncertainties caused by comparison with manual gauging due to reference point movement or bottom movement of the tank are eliminated.

By locating the invention with the gauge well of the tank, the invention can provide multiple measurements at the same single location where manual measurements are taken and greatly increase the verifiability of the monitoring function.

With this alignment, the invention can automatically measure all the values that are measured manually from the gauge well so that comparisons can be made of many variables at the same time the manual samplings by the gauge well are occurring.

Examples of samplings and measurement values can include: changes in a fluid level, temperatures of the fluid, fluid density, and a percentage of water content in a hydrocarbon fluid.

Tank samplings and measured values include: level and temperature of the fluid and fluid density. The alignment of the invention with the gauge well of the tank can allow the measured values from the invention to be compared and calculated with the manual gauge well samplings and readings, which can improve the verification ability and consistency of the measurement values.

Figure 1:
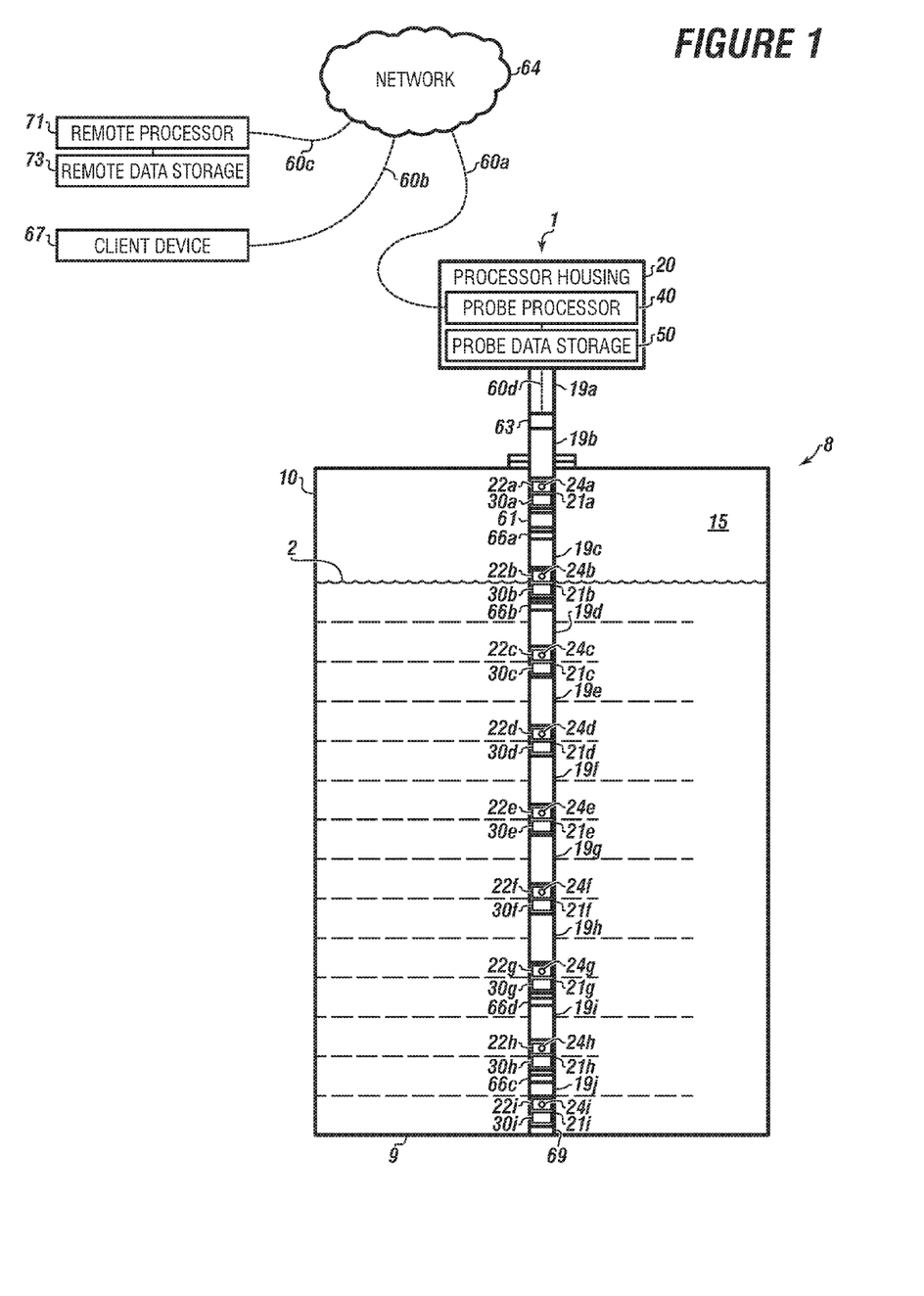
FIG. 1 is a cross sectional view of a probe according to one or more embodiments.

Turning now to the Figures, FIG. 1 shows a probe for use in a tank according to one or more embodiments.

In embodiments, the probe 1 can have no moving parts for use in the tank 8. The tank can have a floor 9 and at least one wall 10. In this embodiment, the tank is shown with a cylindrical wall.

The probe 1 can be configured for continuous measurement of a fluid 2 while the probe is immersed in that fluid. The fluid 2 can be a combination of liquid and vapor. The tank can have a vapor space 15 above the fluid in the tank.

The probe 1 can have a processor housing 20 and a plurality of pressure transducers 22a-22i. In embodiments, each pressure transducer can have a diaphragm 24a-24i.

Each pressure transducer can be configured for continuous pressure measurement through direct contact with the fluid 2 in the tank 8.

The probe 1 can have a plurality of temperature sensors 30a-30i, wherein each of the temperature sensors can be contained in one of the pressure transducers 22a-22i or in one of the sensor housings 21a-21i.

Each temperature sensor can be configured for continuous temperature measurement of the fluid 2 in the tank 8.

The processor housing 20 can have a probe processor 40 that can be electrically connected to the plurality of pressure transducers and to the plurality of temperature sensors and electronically connected to a network 64 with bidirectional signal 60a-60d.

A probe data storage 50 can also be in the processor housing 20. The probe data storage 50 can be in bidirectional communication with the probe processor 40.

The term "data storage" refers to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals.

The probe data storage 50 can be computer readable medium with computer instructions for instructing the probe processor to control the plurality of temperature sensors and the plurality of pressure transducers to produce a bidirectional signal 60a to the network and to produce a bidirectional signal 60d to the plurality of temperature sensors and the plurality of pressure transducers.

A temperature and pressure transducer 61 can be located in the vapor space 15 of the tank 8. In embodiments, more than one temperature and pressure transducer can be used.

A plurality of conduits 19a-19j can be used for connecting the processor housing 20 with the sensor housings 21a-21i. The conduits can extend to a bottom of the probe. In embodiments, the bottom of the probe can be proximate or within inches, such as 1 inch to 30 inches of the floor 9 of the tank 8.

A plurality of switches 66a-66d can be located in the tank 8. Each switch can detect liquid levels, compare detected liquid levels to a preset level in the switch, and then provide a notification signal to a client device 67, the probe processor 40 or both the client device and the probe processor when the liquid exceeds or fails to meet the preset level in the switch.

An external sensor 63 can be disposed outside of the tank 8. The external sensor can be electrically connected to the probe processor 40.

The external sensor 63 can be configured to measure ambient pressure and ambient temperature outside the tank.

The external sensor 63 can provide signals to the probe processor 40. The probe processor can use computer to compare the ambient pressure and temperature measured outside the tank by the external sensor to measured pressure and temperature inside the tank measured by the plurality of pressure transducers and the plurality of temperature sensors for gas blanket monitoring and asset protection of the tank 8.

The probe 1 is shown communicating using the bidirectional signals 60a and 60d with the network 64. Some of the bidirectional signals 60b can be further transmitted to the network 64 to a client device 67 and commands and data can be transmitted from the client device 67 to the network 64 for transmission to the probe processor 40.

A remote processor 71 can be in communication with the probe processor 40 through the network 64. The remote processor can be depicted in communication with bidirectional signals 60c to the network for communication with the probe processor.

The remote processor 71 can be further communicating with a remote data storage 73.

A compound containing sulfur detector 69 can be in communication with the probe processor 40 for detecting compounds containing sulfur. Although the compound containing sulfur detector 40 is shown to be proximate a bottom or the floor 9 of the tank 8, the compound containing sulfur detector 69 can also be located in the vapor space 15.

The compound containing sulfur detector can be in the fluid in the tank, in vapor space in the tank, or mounted external to the tank.

The probe processor can compute compound containing sulfur concentration for protection of personnel or for estimation of quality of crude oil.

Figure 2:
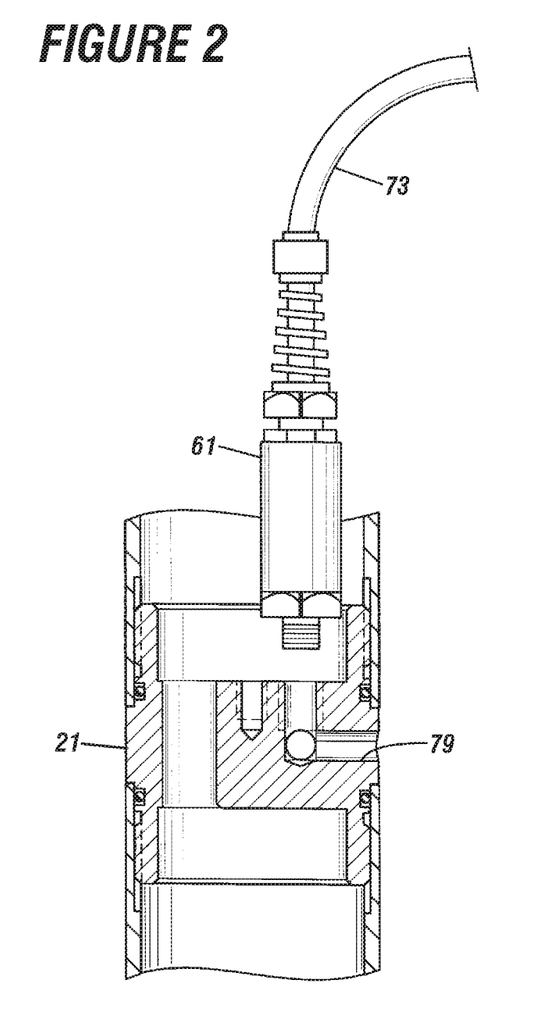
FIG. 2 shows a detail of a sensor housing according to one or more embodiments.

FIG. 2 shows a detail of the sensor housing 21 in partial cross section according to one or more embodiments.

Output leads 73 are shown from the temperature and pressure transducer 61. The temperature and pressure transducer 61 can be disposed partially in the sensor housing 21. In embodiments, to operate the temperature and pressure transducer 61, a portion of the temperature and pressure transducer can be external of the sensor housing.

A channel 79 can be formed in the sensor housing 21. The channel 79 can have a plurality of inclined surfaces that can enable the fluid from the tank to contact with the temperature and pressure transducer 61.

Figure 3:
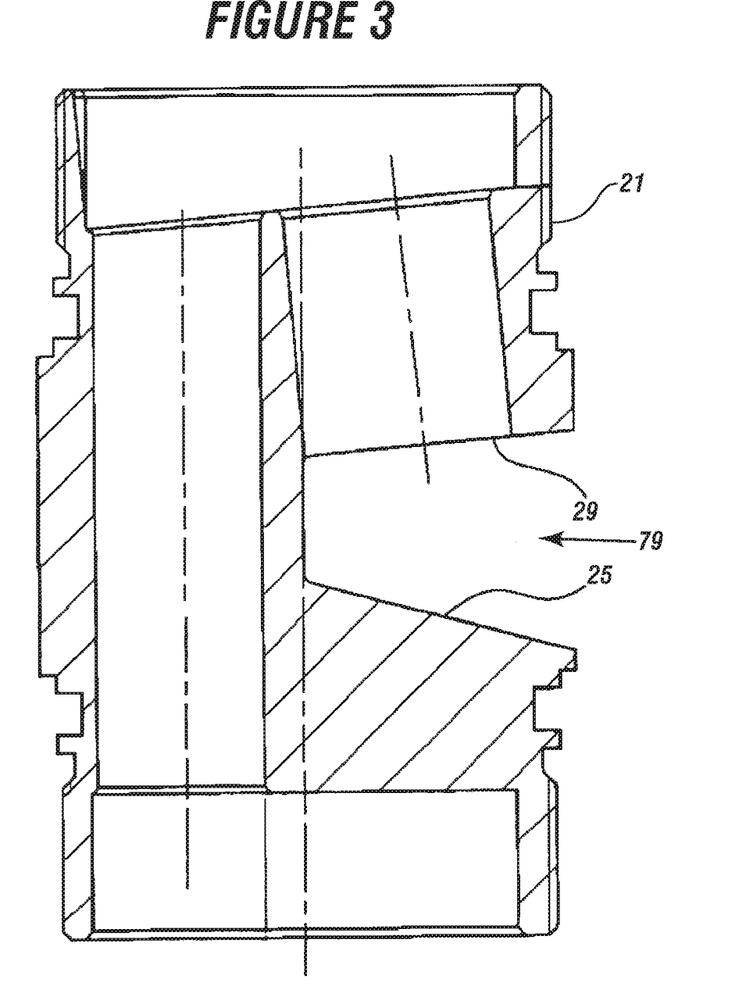
FIG. 3 is a detailed view of a channel of the sensor housing according to one or more embodiments.

FIG. 3 is a detailed view of a channel of the sensor housing according to one or more embodiments.

In this embodiments, the probe can have two inclined surfaces in the sensor housing 21, shown as a first surface 25 and a second surface 29 that can form the channel 79. Each inclined surface can have a slope from 2 degrees to 50 degrees.

In embodiments, a plurality of inclined surfaces can be used on one side of the channel 79. The channel 79 can enable the fluid from the tank to contact a pressure transducer or a temperature sensor in the sensor housing or a combination pressure and sensor transducer in the sensor housing.

In embodiments, one inclined surface can be formed on a side of the channel 79.

Figure 4:
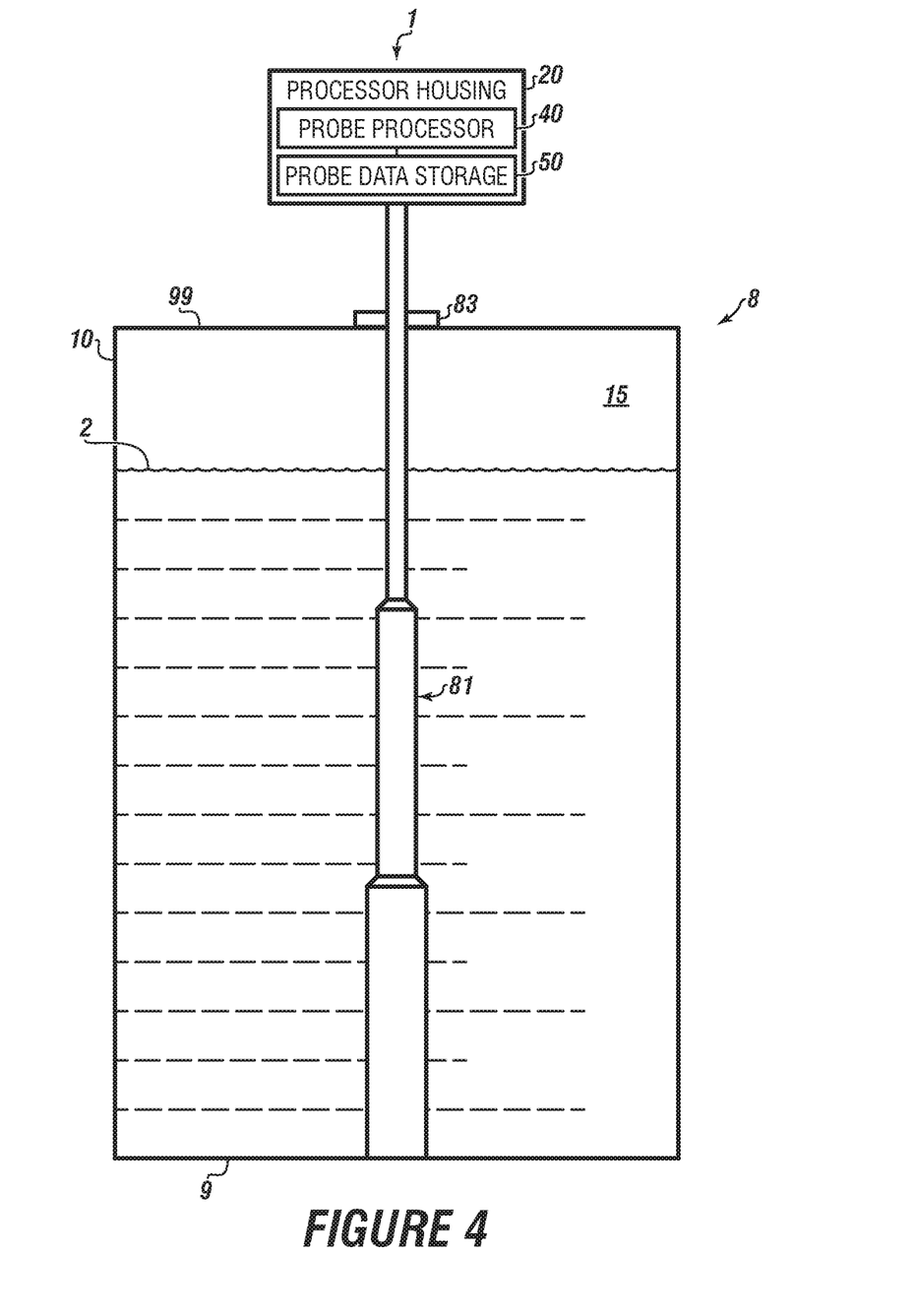
FIG. 4 shows the probe with an outer surface in a stepped configuration according to one or more embodiments.

FIG. 4 shows the probe with an outer surface in a stepped configuration according to one or more embodiments.

The probe 1 is shown with an outer surface 81 formed in a sequential stepped configuration as three segments, wherein each segment can expand at least 10 percent in diameter sequentially from an adjacent segment.

The probe 1 can have a tank movement measuring device 83 connected to a roof 99 of the tank 8 with the fluid 2 and the vapor space 15. The tank 8 can have at least one wall 10, shown here as a cylindrical tank, and a floor 9. The tank movement measuring device 83 can be mounted external of the tank 8.

The tank movement measuring device 83 can be electronically connected to the probe processor 40 in the processor housing 20 or the remote processor via the network. The tank movement measuring device can provide signals that can be stored in the remote processor data storage. The tank movement measuring device 83 can communicate with the probe processor 40 or a display for an operator. The tank movement measuring device can measure and display movement due to flexing of the floor 9 of the tank 8 or due to flexing of the roof 99 of the tank 8. The display can be a local display, a remote display, or combinations thereof.

The tank movement measuring device 83 can measure when the probe has moved due to the flexing of the floor 9 of the tank 8 with the fluid 2 or flexing of the roof 99 of the tank with the vapor space 15 relative to the floor 9. The tank movement measuring device can transmit those measurements to the probe data storage 50 either wirelessly or in a wired communication for further notification to the display associated with the probe processor 40 or the remote processor via the network or the client device via the network.

Figure 5A:
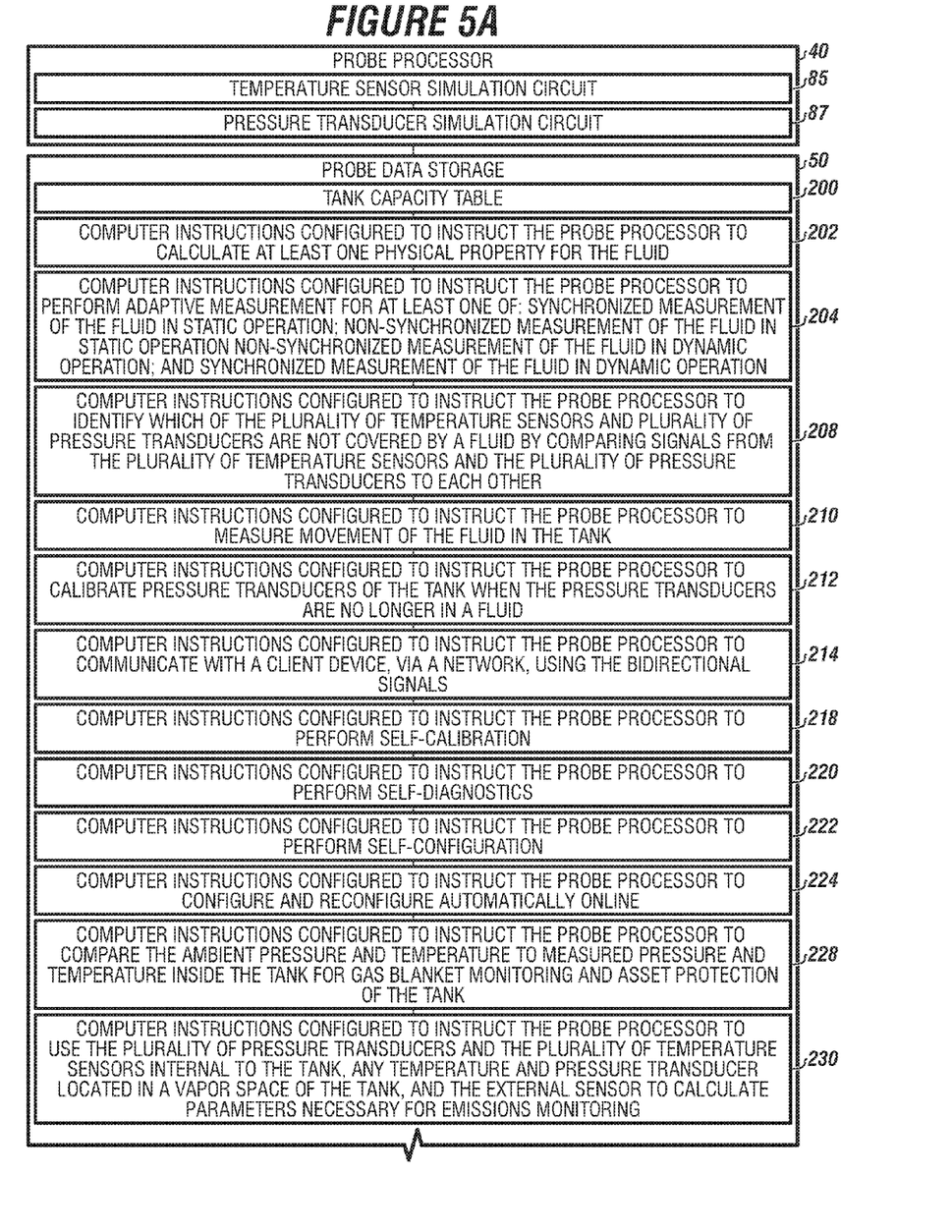
FIGS. 5A and 5B depict a probe processor and a probe data storage according to one or more embodiments.
Figure 5B:
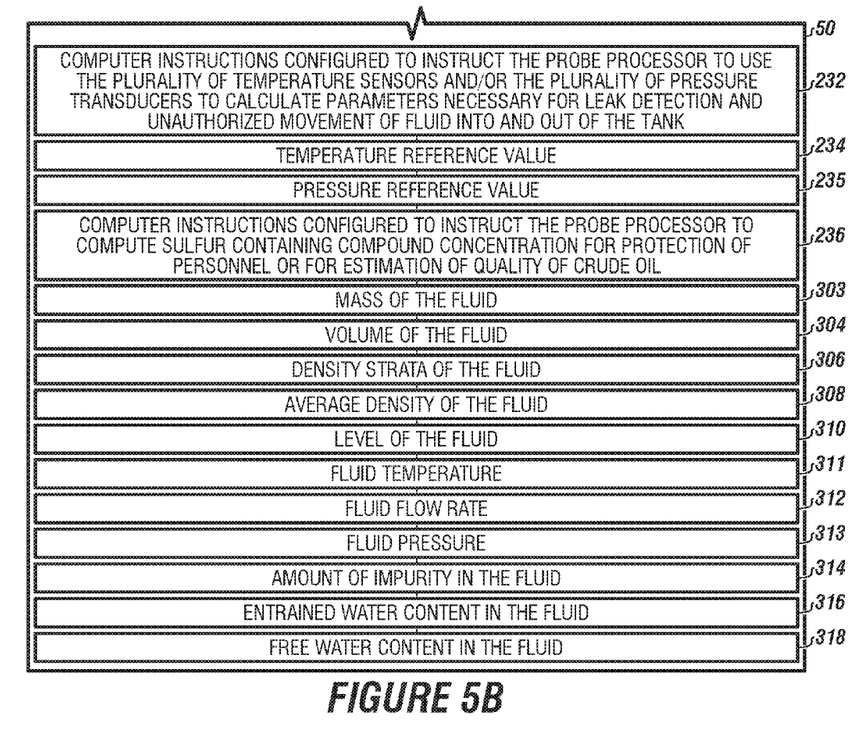

FIGS. 5A and 5B depict a probe processor and a probe data storage according to one or more embodiments.

In embodiments, the probe processor 40 can have a temperature sensor simulation circuit 85 and a pressure transducer simulation circuit 87.

The probe data storage 50 can be connected to the probe processor 40.

The temperature sensor simulation circuit 85 can be for automatically calibrating the probe processor and can use a temperature reference value 234 for calibration. The temperature reference value 234 can be shown in the probe data storage 50.

The pressure transducer simulation circuit 87 can be for automatically calibrating the probe processor. The pressure transducer simulation circuit can use a pressure reference value 235 for calibration. The pressure reference value 235 can be shown in the probe data storage 50.

The probe data storage 50 can contain a tank capacity table 200, which can show capacities and/or volumes in a tank for various fluid levels as measured from a reference gauge point.

The probe data storage can contain computer instructions 202 configured to instruct the probe processor to calculate at least one physical property for the fluid.

The physical properties can be stored in the probe data storage and can include but are not limited to: a mass of the fluid 303, a volume of the fluid 304, a density strata of the fluid 306, an average density of the fluid 308, a level of the fluid 310, a fluid temperature 311, a fluid flow rate 312, a fluid pressure 313, an amount of impurity in the fluid 314, an entrained water content in the fluid 316, and a free water content in the fluid 318.

The probe data storage can contain computer instructions 204 to instruct the probe processor to perform adaptive measurement for at least one of: synchronized measurement of the fluid in static operation, non-synchronized measurement of the fluid in static operation, non-synchronized measurement of the fluid in dynamic operation, and synchronized measurement of the fluid in dynamic operation.

The probe data storage can contain computer instructions 208 configured to instruct the probe processor to identify which of the plurality of temperature sensors and the plurality of pressure transducers are not covered by a fluid by comparing signals from the plurality of temperature sensors and the plurality of pressure transducers to each other.

The probe data storage can contain computer instructions 210 configured to instruct the probe processor to measure movement of the fluid in the tank.

The probe data storage can contain computer instructions 212 configured to instruct the probe processor to calibrate pressure transducers of the tank when the pressure transducers are no longer in a fluid.

The probe data storage can contain computer instructions 214 configured to instruct the probe processor to communicate with a client device via a network by using the bidirectional signals.

The probe data storage can contain computer instructions 218 configured to instruct the probe processor to perform self-calibration.

The probe data storage can contain computer instructions 220 configured to instruct the probe processor to perform self-diagnostics.

The probe data storage can contain computer instructions 222 configured to instruct the probe processor to perform self-configuration.

In embodiments, the probe data storage can have at least one computer instruction configured to instruct the probe processor to preform self-calibration, perform self-diagnostics, perform self-configuration, or various combinations thereof.

The probe data storage can contain computer instructions 224 configured to instruct the probe processor to configure and reconfigure automatically online.

The probe data storage can contain computer instructions 228 configured to instruct the probe processor to compare the ambient pressure and temperature to measured pressure and temperature inside the tank for gas blanket monitoring and asset protection of the tank.

The probe data storage can contain computer instructions 230 configured to instruct the probe processor to use the plurality of pressure transducers and temperature sensors internal to the tank, any temperature and pressure transducer located in a vapor space of the tank and the external sensor to calculate parameters necessary for emissions monitoring.

The probe data storage can contain computer instructions 232 configured to instruct the probe processor to use the plurality of temperature sensors and/or the plurality of pressure transducers to calculate parameters necessary for leak detection and unauthorized movement of fluid into and out of the tank.

The temperature sensor simulation circuit's temperature reference value 234 and the pressure transducer simulation circuit's pressure reference value 235 are shown in the probe data storage 50.

The probe data storage can contain computer instructions 236 configured to instruct the probe processor to compute compounds containing sulfur concentration for protection of personnel or for estimation of quality of crude oil as mentioned earlier.

Figure 6:
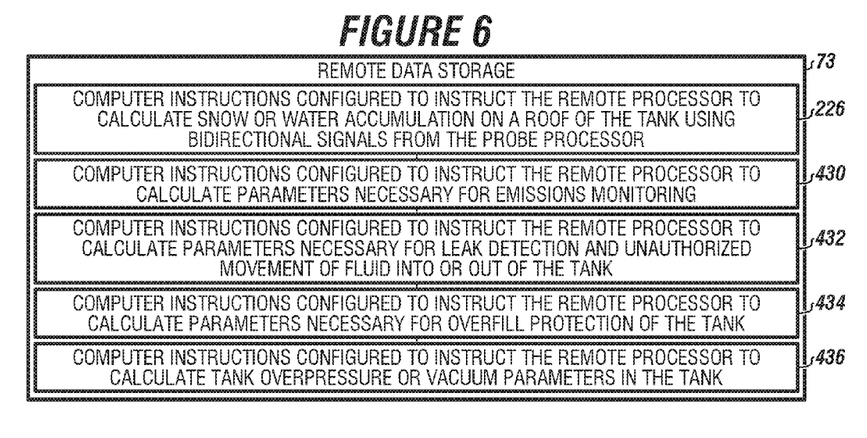
FIG. 6 depicts a remote data storage according to one or more embodiments.

FIG. 6 depicts a remote data storage according to one or more embodiments.

The remote data storage 73 can contain computer instructions 226 configured to instruct the remote processor to calculate snow or water accumulation on a roof of the tank using bidirectional signals from the probe processor.

The remote data storage can contain computer instructions 430 configured to instruct the remote processor to calculate parameters necessary for emission monitoring.

The remote data storage can contain computer instructions 432 configured to instruct the remote processor to calculate parameters necessary for leak detection and unauthorized movement of fluid into or out of the tank.

The remote data storage can contain computer instructions 434 configured to instruct the remote processor to calculate parameters necessary for overfill protection of the tank.

The remote data storage can contain computer instructions 436 configured to instruct the remote processor to calculate tank overpressure or vacuum parameters in the tank.

In embodiments, the processor housing can be weatherproof or explosion proof.

While these embodiments have been described with emphasis on the embodiments, it can be understood that within the scope of the appended claims, the embodiments might be practiced other than as specifically described herein.

What is claimed is:

1. A probe with no moving parts for use in a tank, the tank having a floor and at least one wall, the probe configured for continuous measurement of a fluid while immersed in the fluid, wherein the probe comprises:
   a) a processor housing;
   b) a plurality of pressure transducers, each pressure transducer having a diaphragm, each pressure transducer configured for continuous pressure measurement through direct contact with the fluid in the tank;
   c) a plurality of temperature sensors, each temperature sensor contained in either one of the pressure transducers or in a sensor housing, each temperature sensor configured for continuous temperature measurement of the fluid in the tank;
   d) a computer processor in the processor housing, the computer processor electrically connected to the plurality of pressure transducers and to the plurality of temperature sensors; and
   e) a probe data storage in the processor housing, the probe data storage in communication with the computer processor, the probe data storage being a non-transitory computer readable medium containing computer instructions stored thereon for causing the computer processor to control the plurality of temperature sensors and the plurality of pressure transducers to produce bidirectional signals to the plurality of temperature sensors and the plurality of pressure transducers to a network, the probe data storage containing:
      (i) a tank capacity table showing capacities and/or volumes in the tank for various fluid levels as measured from a reference gauge point;
      (ii) computer instructions configured to instruct the computer processor to calculate at least one physical property for the fluid, the physical property selected from the group consisting of:
         1. a mass of the fluid;
         2. a volume of the fluid;
         3. a density strata of the fluid;
         4. an average density of the fluid;
         5. a level of the fluid;
         6. a fluid temperature;
         7. a fluid flow rate;
         8. a fluid pressure;
         9. an amount of impurity in the fluid;
         10. an entrained water content in the fluid; and
         11. a free water content in the fluid;
      (iii) computer instructions configured to instruct the computer processor to perform adaptive measurement for at least one of:
         1. a synchronized and non-synchronized measurement of the fluid in static operation; or
         2. a non-synchronized and synchronized measurement of the fluid in dynamic operation;
      (iv) computer instructions configured to instruct the computer processor to identify which of the plurality of temperature sensors and the plurality of pressure transducers are not covered by the fluid by comparing signals from the plurality of temperature sensors and the plurality of pressure transducers to each other;
      (v) computer instructions configured to instruct the computer processor to measure movement of the fluid in the tank;
      (vi) computer instructions configured to instruct the computer processor to calibrate the plurality of pressure transducers of the tank when the plurality of pressure transducers are no longer in the fluid; and
      (vii) computer instructions configured to instruct the computer processor to communicate with a client device via the network using the bidirectional signals; and
   wherein the computer processor comprises a temperature sensor simulation circuit with a temperature reference value in the probe data storage and a pressure transducer simulation circuit in the computer processor with a pressure reference value in the probe data storage, the temperature sensor simulation circuit and the pressure transducer simulation circuit for calibrating the computer processor for measuring temperature or pressure.

2. The probe of claim 1, comprising at least one temperature and at least one pressure transducer located in a vapor space of the tank.

3. The probe of claim 2, comprising an external sensor outside of the tank and electrically connected to the computer processor, the external sensor configured to measure ambient pressure and ambient temperature outside the tank, the external sensor providing signals to the computer processor, the computer processor using computer instructions in the data storage, the computer instructions configured to instruct the computer processor to compare measured ambient pressure and temperature to measured pressure and temperature inside the tank for gas blanket monitoring and asset protection of the tank.

4. The probe of claim 3, comprising computer instructions in the probe data storage, the computer instructions configured to instruct the computer processor to use the plurality of pressure transducers and the plurality of temperature sensors internal to the tank, any temperature sensor and any pressure transducer located in the vapor space of the tank and the external sensor to calculate the parameters necessary for emissions monitoring.

5. The probe of claim 2, further comprising at least one compound containing sulfur detector in communication with the computer processor for detecting compounds containing sulfur and computer instructions in the probe data storage configured to instruct the computer processor to compute compound containing sulfur concentrations for protection of personnel or for estimation of quality of crude oil, wherein the compound containing sulfur detector is in liquid in the tank, in the vapor space in the tank or mounted external to the tank.

6. The probe of claim 1, wherein an outer surface of the probe expands in a stepped configuration, increasing at least ten percent in diameter.

7. The probe of claim 1, comprising a channel in the sensor housing to provide contact with the fluid from the tank to at least one of the plurality of temperature sensors and at least one of the plurality of pressure transducers.

8. The probe of claim 7, comprising a plurality of inclined surfaces on at least one side of the channel, the plurality of inclined surfaces enabling the fluid to contact with at least one of: the plurality of pressure transducers, the plurality of temperature sensors, or both the plurality of pressure transducers and the plurality of temperature sensors.

9. The probe of claim 1, comprising a plurality of switches in the tank that provide a notification signal to the computer processor, the network, or both the computer processor and the network when the fluid exceeds or fails to meet a preset level.

10. The probe of claim 1, comprising a tank movement measuring device connected to the probe for displaying and measuring probe movement due to flexing of the floor of the tank or due to flexing of a roof of the tank.

11. The probe of claim 1, wherein the probe data storage comprises at least one of:
   a) computer instructions configured to instruct the computer processor to perform self-calibration;
   b) computer instructions configured to instruct the computer processor to perform self-diagnostics; and
   c) computer instructions configured to instruct the computer processor to perform self-configuration.

12. The probe of claim 1 wherein the probe data storage comprises computer instructions configured to instruct the computer processor to configure and reconfigure automatically online.

13. The probe of claim 1, comprising a remote computer processor bidirectionally connected to the computer processor via the network, the remote computer processor further comprising a remote data storage comprising a non-transitory computer readable medium containing computer instructions stored therein for causing the remote computer processor to perform at least one of:
   a) calculation of snow or water accumulation on a roof of the tank using the bidirectional signals;
   b) calculation of parameters necessary for emissions monitoring;
   c) calculation of parameters necessary for leak detection and unauthorized movement of the fluid into or out of the tank;
   d) computer instructions configured to instruct the remote processor to calculate calculation of parameters necessary for overfill protection of the tank; and
   e) calculation of tank overpressure or vacuum parameters in the tank.

14. The probe of claim 1, comprising in the probe data storage computer instructions configured to instruct the computer processor to use the plurality of temperature sensors, the plurality of pressure transducers, or both the plurality of temperature sensors and the plurality of pressure transducers to calculate the parameters necessary for leak detection and unauthorized movement of the fluid into and out of the tank.

15. The probe of claim 1, wherein the processor housing is weatherproof or explosion proof.

16. The probe of claim 1, comprising a plurality of conduits connecting the processor housing with the sensor housing and extending to a bottom of the probe.

* * * * *